United States Patent
Rubinfeld et al.

(10) Patent No.: US 6,436,435 B1
(45) Date of Patent: Aug. 20, 2002

(54) LIPOSOME FORMULATION OF 5 β STEROIDS

(75) Inventors: Joseph Rubinfeld, Danville; Elliott L. Fineman, Kensington, both of CA (US)

(73) Assignee: Super Gen, Inc., Dublin, CA (US)

( * ) Notice: Subject to any disclaimer, the term of this patent is extended or adjusted under 35 U.S.C. 154(b) by 0 days.

(21) Appl. No.: 09/300,819

(22) Filed: Apr. 27, 1999

Related U.S. Application Data

(63) Continuation of application No. 08/989,208, filed on Dec. 11, 1997, now abandoned, which is a continuation of application No. 08/542,083, filed on Oct. 12, 1995, now abandoned.

(51) Int. Cl.$^7$ .............................. A61K 9/127; A61F 2/00
(52) U.S. Cl. ...................................... 424/450; 424/423
(58) Field of Search ......................................... 424/450

(56) References Cited

U.S. PATENT DOCUMENTS

| | | |
|---|---|---|
| 4,507,289 A | 3/1985 | Coleman et al. ............ 514/170 |
| 4,518,595 A | 5/1985 | Coleman et al. ............ 514/178 |
| 4,522,803 A | 6/1985 | Lenk et al. .................. 424/1.1 |
| 4,588,578 A | 5/1986 | Fountain et al. ............. 424/1.1 |
| 4,666,898 A | 5/1987 | Coleman et al. ............ 514/177 |
| 4,861,580 A | 8/1989 | Janoff et al. ................. 424/1.1 |
| 5,006,517 A | 4/1991 | Bradlow et al. ............. 514/178 |
| 5,041,287 A | 8/1991 | Driggers et al. .............. 424/81 |
| 5,231,112 A | 7/1993 | Janoff et al. ................. 514/401 |
| 5,330,689 A | 7/1994 | Janoff et al. ................. 264/4.3 |
| 5,573,779 A | 11/1996 | Sato et al. .................... 424/450 |
| 5,597,797 A | 1/1997 | Clark ........................... 514/12 |
| 6,015,576 A * | 1/2000 | See et al. .................... 424/450 |

FOREIGN PATENT DOCUMENTS

| | | | |
|---|---|---|---|
| DE | 3626421 A1 | 2/1988 | ............ C07K/7/10 |
| EP | 0 139 554 A1 | 8/1984 | ............ C07K/9/00 |
| WO | 86/00238 | 1/1986 | ............ B01D/13/00 |
| WO | 87/00043 | 1/1987 | ............ A61K/9/00 |
| WO | 94/04155 | 3/1994 | ........... A61K/31/56 |

OTHER PUBLICATIONS

"Ambisome" Merck Index, 1996.*
Bangham et al., Diffusion of Univalent Ions Across the Lamellae of Swollen Phospholipids, *J. Mol. Biol.*, 13, 238–252 (1965).
Papahadjopoulos et al., "Phospholipid Model Membranes" *Biochem. Biophys. Acta.*, 13, 624–638 (1968).
Yen et al., "Prevention of Obesity in A$^{vy}$/a Mice by Dehydroepiandrosterone", *Lipids*, vol. 12, No. 5, pp. 409–413, Jan. 5, 1977.
Coleman et al., "Diabetes–Obesity Syndromes in Mice", *Diabetes*, 31 (Suppl. 1), pp. 1–6, Apr. 1982.
Vincent et al., "Steroid–Lipid Interactions in Sonicated Dipalmitoyl Phosphatidyl Choline Vesicles: A Steady–State and Time–Resolved Flurescene Anisotropy Study With All Trans–1,6–Diphenyl–1,3,5–Hexatriene As Probe," *Biological and Biophysical Research Communications*, vol. 113, No. 3, 1983, pp. 799–810; Jun. 29, 1983.
Poznansky et al., "Biological Approaches to the Controlled Delivery of Drugs: A Critical Review", Pharmacological Reviews, vol. 36, No. 4, pp. 277–335, 1984.
Coleman et al., "Therapeutic Effects of Dehydroepiandrosterone Metabolics in Diabetes Mutant Mice", *Endocrinology*, 115, No. 1, 239–243, 1984.
Coleman, "Antiobesity Effects of Etiocholanolones in Diabetes (db), Viable Yellow (A$^{vy}$), and Normal Mice", *Endocrinology*, 117, No. 6, pp. 2279–2283, 1985.
Brewster, et al., "Improved Delivery through Biological Membranes XXXI: Solubilization and Stabilization of an Estradiol Chemical Delivery System by Modified β–Cyclodextrins," *Journal of Pharmaceutical Sciences*, vol. 77, No. 11, Nov. 1988.
Weiner et al. Liposomes As A Drug Delivery System, *Drug Development and Industrial Pharmacy*, 15(10), pp. 1523–1554, 1989.
Zumoff et al., "A Randomized Double–Blind Crossover Study of the Antiobesity Effects of Etiocholanedione", *Obesity Research*, vol. 2, No. 1 (Jan. 1994).
Zhang et al. "Positional Cloning of the Mouse Obese Gene and its Human Homologue", *Nature*, 372, pp. 425–432, Dec. 1, 1994.
Murakami et al., "Cloning of Rat Obese cDNA and its Expression in Obese Rats", *Biochem. Biophys. Res. Comm.*, 209 (3), pp. 944–952, Apr. 26, 1995.
Considine et al., "Evidence Against Either a Premature Stop Codon or the Absence of Obese Gene mRNA in Human Obesity", *J. of Clin. Inv.*, 95 (6), pp. 2986–2988, Jun. 1995.
Pelleymounter et al. "Effects of the Obese Gene Product on Body Weight Regulation in ob/ob Mice", *Science*, 269, pp. 540–543, Jul. 28, 1995.
Halaas et al., "Weight–Reducing Effects of the Plasma Protein Encoded by the Obese Gene", *Science*, 269, pp. 543–546, Jul. 28, 1995.
Campfield et al., "Recombinant Mouse OB Protein: Evidence for a Peripheral Signal Linking Adiposity and Central Neural Networks", *Science*, 269,pp. 546–549, Jul. 28, 199).

* cited by examiner

Primary Examiner—James M. Spear
(74) *Attorney, Agent, or Firm*—Shirley Chen; Wilson Sonsini Goodrich & Rosati

(57) ABSTRACT

Liposome preparations which comprise a lipid, or lipid like compound and a 5β steroid, DHEA or an organic acid derivative of the 5β steroid or DHEA are described. The lipsome may also include an entraped aqueous portion which comprises dissolved therein the expression product of the ob gene. Methods for treating conditions including obesity,hypercorticoidism and diabetes using the liposome preparations are also claimed.

18 Claims, No Drawings

LIPOSOME FORMULATION OF 5 β STEROIDS

RELATIONSHIP TO COPENDING APPLICATIONS

This application is a continuation of application Ser. No. 08/989,208 filed Dec. 11, 1997, abandoned which is a continuation of application Ser. No. 08/542,083, filed on Oct. 12, 1995 (now abandoned).

FIELD OF THE INVENTION

The invention relates to liposome preparations capable of enhancing the delivery of DHEA and 5β steroids to the liver. Additionally the liposomal preparation may also be used to transport an antiobesity peptide or protein in an included aqueous phase.

BACKGROUND OF THE INVENTION

Liposomes are completely closed lipid bilayer membranes containing an entrapped aqueous volume. Liposomes may be unilamellar vesicles (possessing a single bilayer membrane) or multi lamellar vesicles (onion-like structures characterized by multiple membrane bilayers, each separated from the next by an aqueous layer). The bilayer is composed of two lipid monolayers having a hydrophobic tail region and a hydrophilic head region. The structure of the membrane bilayer is such that the hydrophobic (nonpolar) tails of the lipid monolayers orient toward the center of the bilayer while the hydrophilic heads orient toward the aqueous phase.

The liposomes originally prepared by Bangham et al., *J. Mol Biol.*, 13,238–252(1965) were produced by suspending phospholipids in an organic solvent and evaporating the mixture to dryness leaving a phospholipid film on the surface of the vessel. An aqueous phase was added, the mixture was allowed to swell and was dispersed by mechanical means. Liposomes resulting from the procedure consisted of multi lamellar vesicles (MLVs). Subsequently, Papahadjopoulos et al., *Biochim. Biophys. Acta.*, 13,624–638(1968) developed small unilamellar vesicles by sonicating the mixture.

LUVETS, unilamellar vesicles extruded under pressure through a membrane filter are disclosed in Cullis et al., PCT Application No. Wo 86/00238, published Jan. 16, 1986, which is herein incorporated by reference. Luvets usually range from about 100 NM to about 500 NM in diameter.

Liposomes having substantially equal lamellar-solute distribution are denominated stable plurilamellar vesicles (SPLV) as defined in U.S. Pat. No. 4,522,803 to Lenk et al., Monophasic vesicles are described by Fountain, et al. in U.S. Pat. No. 4,588,578. Frozen and thawed multi lamellar vesicles (FATML V), which are produced by exposing vesicles to at least one freeze and thaw cycle are described in Bally et al., PCT Publication No. 87/00043 published Jan. 15, 1987. The forgoing references are incorporated herein by reference for the teaching of preparation and various uses of liposomes.

With respect to the lipids used in the formation of liposomes, in general the hydrophobic non-polar regions of lipid monolayers orient toward the center of the bilayer while the hydrophilic regions orient toward the aqueous phase. The aqueous phase including any product dissolved therein may be partially or fully enclosed by the membrane bilayer. Examples of lipids are the phospholipids such as phosphatidylcholine (PG), egg phoshpatidylcholine (EPG), phosphatidylserine, phoshpatidylglycerol, phoshpatidylinositol, phosphatidic acid, sphingomyelin and the like alone or in combination and particularly in hydrogenated or saturated form of the carbon chain. The phospholipids can be synthetic or derived from natural sources. Synthetic phospholipids include dymyristoylphoshpatidylcholine, and dimyristoylphosphatidylglycerol.

Alpha tocopherol-based bilayer vesicles are disclosed in Janoff et al.,, U.S. Pat. No. 5,041,287, Janoff al., U.S. Pat. No. 5,231,112, and Janoff et al., U.S. Pat. No. 5,330,689, which are all herein incorporated by reference. These vesicles are formed from organic acid derivatives of alpha tocopherol which are capable of forming of completely closed bilayers in aqueous solutions.

Liposomes prepared using salt forms of cholesterol hemisuccinate are disclosed in Janoff et al., U.S. Pat. No. 5,231,112, herein incorporated by reference. Peptides and proteins that appear to have an impact upon the tendency of a mammal to become obese and to gain weight in excess of normal are now known. A protein product of the recombinant gene ob in mice as well as its human homologue have been disclosed in Y. Zhang et al, *Nature,* 372,425 (1994). In addition, the homologous gene in rats, apparently without mutations, has been cloned as disclosed in T. Murakami and K. Shima, *Biochemical amid Biophysical Research Commiunications,* 209 (3), 944 (1995). R. A. Considine et al., *Journal of Clinical Investigation,* 95 (6), 2986 (1995) disclose the isolation of the full coding region of the ob gene from a human adipocyte cDNA library and translation of the cloned sequence resulting in a protein having the predicted amino acid sequence of the normal protein. M. A. Pelleymounter et al., *Science,* 269, 540 (1995), J. L. Halaas et. al., *Science,* 269, 543 (1995), and L. A. Campfield, et al., *Science,* 269, 546 (1995) disclose that this protein has weight reducing effects when administered parenterally to congenitally obese mice carrying the ob ob mutation. In addition serum insulin and glucose levels, usually markedly elevated above normal in ob·ob mice, were significantly reduced in a dose dependent fashion and were normalized to the level typically seen in the non-mutant mice at the highest dose tested (10 mg/kg per day). M. A. Pelleymounter et al., further disclose that the protein may be dissolved in phosphate buffered saline at pH 7.4 and administered intraperitoneal injection.

The steroid dehydroepiandrosterone (3-β-hydroxy-androst-5-en-17-one, DHEA) and its sulfate derivatives are major steroid adrenal secretory products in humans. DHEA is metabolized to testosterone (17-β-hydroxy-androst-4-en-3-one) and estradiol (estra-1,3,5 (10)-triene-3,17-diol), two major sex hormones in humans. Other metabolites of DHEA include α ET and β-ET. They were considered to be inert metabolic end products which were merely conjugated as glucuronides or sulfates and excreted into the urine. α ET is a major metabolite of DHEA, and in normal individuals, is excreted in the urine in amounts of about 3–5 mg per day, whereas β ET is a minor metabolite in man.

The effect of these compounds upon obesity and diabetes is summarized as follows. Yen et al., *Lipids.* 12, 409 (1977) disclosed that DHEA administered by a variety of routes decreased the rate of weight gain in a strain of genetically obese mice. DHEA treatment markedly reduced the development of diabetes in both genetically obese and diabetic mice and maximal benefit was observed when DHEA was ingested according to Coleman et al., *Diabetes* 31:80 (1982). Coleman et al., *Endocrinology,* 115, 239 (1984) showed that α ET and β ET reduce blood sugar, increased plasma insulin concentrations and provided a protective effect on the pancreas as demonstrated by increased granulation of islet β cells. Moreover, α ET and β ET but not androsterone or epiandrosterone, were four times more effective than DHEA in preventing development of diabetes in C57BL/KsJ-db/db diabetic mice. Coleman et a/., U.S. Pat. No. 4,518,595 showed that oral administration of DHEA restored hyperglycemia to normal levels and improved glucose tolerance even in severely diabetic mammals. In U.S. Pat. No. 4,507,289 Coleman taught the use of α ET and β ET and an estrogen for the treatment of diabetes, obesity syndromes and associated hypercorticoidism.

Coleman,, Endocrinology, 117, 2279 (1985) disclosed that α ET and β ET when supplied in the diet have anti-obesity properties, and can prevent and arrest the development of obesity, ad facilitate weight reduction after obesity in diabetic genetically obese mice. U.S. Pat. No. 4,666,898 to Coleman and Applezweig disclosed the use of Etiocholanolones in the treatment of obesity, diabetes and other symptoms of hypercorticoidism. B. Zumoff et al., Obesity Research, 2, 13 (1994) disclosed that ED orally administered at a dose of four grams per day yielded significant fat loss in human obese subjects. In a 20 week randomized double-blind cross over study, 14 subjects lost significantly more weight and body fat during treatment with oral ED than during placebo administration. Mean weight loss during ED administration was 2.8±5.5 kilograms which was equivalent to 0.5±0.91 kilograms per week per 100 kilograms of body fat. Dersitometric measurement of body fat content showed that the mean weight loss coincided almost exactly with the mean decrease in body fat content. Over the 10 week period of ED administration, the mean fat loss was about 5% of the initial body fat content. There were no significant subjective or objective side effects of ED administration.

U.S. Pat. No. 5,006,517 to Bradlow, et al., discloses that Prader-Willi Syndrome a congenital disease caused by a chromosomal defect may be treated by administering etiocholanolone or etiocholanolondione to individuals suffering from the syndrome resulting in either weight loss or a decrease in the rate of weight gain in the treated individuals.

While several of the 5β steroids are known to be active in control of obesity and associated diabetic and/or hyper cortical syndrome, the compounds are effective for treatment of these conditions when they are administered orally. By the oral route, the absorption of the 5β steroids is only 5 to 15% as measured by blood levels using various assays. Thus a large portion of the administered drug is never absorbed into the blood stream and the greatest part of the drug that is administered is eliminated in the feces.

A more efficient route of administration for the achievement of high serum concentrations is customary to administer drugs parenterally; however, it has been observed that the 5β steroids do not appear to exert any of their anti-obesity, anti-diabetic or anti-hyper cortical activities when administered by this route. Thus, it would be desirable to have a formulation that would allow parenteral administration of the 5β steroids, preferably by the intravenous (iv) route and which would preserve the anti-obesity, anti-diabetic and anti-hyper cortical activities of these compounds. Considerable saving in the cost of active drug substance for a given response could be achieved thereby.

SUMMARY AND OBJECTS OF THE INVENTION

One aspect of the present invention is directed to providing a composition for inducing increased hepatic availability of therapeutic amounts 5β steroids or DHEA Another aspect of the present invention is direct to a method for treating conditions selected from the group consisting of obesity, diabetes syndrome, diabetes associated hypercorticoidism and combination thereof, and bone marrow suppressive disorders comprising administering to a mammal in need of such treatment a liposomal preparation comprising liposomes comprising an amount of 5β steroid or DHEA or a mixture thereof effective to treat obesity, diabetes or hypercorticoidism and combinations thereof, and bone marrow suppressive disorders.

Yet another aspect of the present invention is directed to providing a composition for increasing the blood level of an anti-obesity peptide or protein. A further aspect of the present invention is directed to providing a composition for treatment of obesity and diabetes associated therewith comprising a liposomal preparation comprising liposomes the lipid portion of said liposomes comprising an amount of 5β steroid or DHEA or a mixture thereof effective to treat obesity, diabetes or hypercorticoidism and combinations thereof and the aqueous portion of said liposomes comprising and amount of an anti-obesity peptide or protein effective to treat obesity and diabetes associated therewith.

DETAILED DESCRIPTION OF THE INVENTION

By 5β steroid is meant 3α-hydroxy-5β-androstane-17-one or α-etiocholanolone (herein after α ET), 3β-hydroxy-5β-androstane-17-one or β etiocholanolone (herein after β ET), and 5β-androstane-3,17-dione or etiocholandione (herein after ED.) In addition certain alkylated derivatives of these 5β steroids are also included in this definition. For example 16-alkylated 5β androstan-3-ol-17-one and 16-alkylated 5β androstan-3,7 diol-17-one which are disclosed in U.S. Pat. No. 4,602,008, herein incorporated by reference, have been shown to be biologically effective as anti-diabetic, anti-obesity and eyhropoietic agents in mammals. These compounds may be esterified at the 3 or 7 positions of the steroid ring structure by conventional means.

In addition other diols of the 17 keto 5-β steroids are commercially available and may be used in the invention and may be esterified at the carbon at which the —OH moiety is attached. Thus, for example 5β- androstan-3α, 11α-diol-17-one, 5β- androstan-3β, 11β-diol-17-one, and 5β- androstan-3α, 11β-diol-17-one, 5β-androstane-11α-ol-3,17-dione, 5β-androstane -11β-ol-3,17-dione, 5β-androstane -3α,16α-diol-17-one are commercially available (Research Plus. Inc, POB 324. Bayonne, N.J. 07002 USA) and may be esterified at the 11 or 16 positions as the case may be, by conventional means to produce the organic acid derivative of the 5β steroids. The organic acid derivative may be converted to the salt for using any appropriate counter ion such as tris.

By "lipid portion of the liposome" is meant the bilayer portion of the liposome which generally is comprised of a molecule having a hydrophobic end and a hydrophilic end, wherein the hydrophobic end generally self associates forming a bilayer in the presence of aqueous media. In the present invention the lipid portion of the liposome may be comprised of any of the lipids disclose herein above such as for example, phosphatidylinositol and sphinzomyelin, or lipid like compounds such as for example the hemisuccinate esters of the 5β steroids, alpha tocopherol and cholesterol and there corresponding salts.

By "aqueous portion of the liposome" is meant the aqueous compartment which is encapsulated in the generally completely closed bilayer membrane which makes up the lipid portion of the liposome. A liposome may have numerous enclosed or encapsulated compartments if the liposome is multi lamellar or a single encapsulated compartment if the liposome is unilamellar.

By "expression product of the ob gene" is meant a protein generally produced from the ob gene or a fragment thereof using a recombinant host cell such as *E. Coli*. In general the gene will be ligated in an expression vector compatible with the host cell and will produce an mRNA transcript of the gene which is subsequently translated or expressed by the host cell into a protein. Frequently the protein is further processed, refolded, cleaved or purified or all of the preceding using chromatograph and other methods. Such further processed refolded cleaved or purified proteins encoded by the ob gene or portions thereof which are active are also included in this definition.

It has been observed by Coleman et. al. that α and β ET when injected im, ip or iv into obese mice does not exert an anti-obesity effect, whereas all three of these compounds when administered orally exert an anti-obesity effect. It is known that a substantial portion of an orally administered drug is absorbed into the blood via the blood vessels of the intestinal tract after oral administration and that a significant portion of the blood draining from the intestines via the mesenteric veins is shunted to liver via the hepatic portal vein. Thus the inventors have reasoned that the biological activity associated with the oral administration of α ET, β ET and ED, but not that associated with iv or other parenteral administration route, particularly the anti- obesity and anti diabetic activities of the 5β steroids results from the activity of the liver on the substantial portion of drug which circulates to the liver following oral administration. Conversely, the absence of anti-obesity and anti-diabetic activity of the 5β steroids following parenteral administration is believed to result from the comparatively small amounts of the 5β steroids reaching the hepatic circulation following parenteral administration.

The inventors have discovered that the amount of 5β steroid reaching the hepatic circulation following parenteral administration can be increased by administering the compound as a component of a liposome. The liposomal preparation according to the invention is trapped by the reticuloendothelial system of which the liver is a part, and the 5β steroid is concentrated in the liver as the liposomes accumulate. In a similar manner, the inventors have the discovered that the compound DHEA can be advantageously administered as a component of a liposome.

The 5β steroids according to the invention may be admixed with lipids which make up the lipophilic envelope of the liposome. In general such lipids are compounds which have a lipophilic region which is hydrophobic and at least one hydrophilic end. Examples of such lipids are rigid lipid, wherein the chains are of a length of about 16 carbon units in which the chains are saturated. Such lipids as diplamitoylphophatidylcholine (DPPC) and distearoylphosphatidylcholine are typical. Also cholesterol hemisuccinate tris (hydroxymetyl)aminomethane ($CHS_{ms}$) is a rigid lipid and may be used as a component of the liposomes according to the invention.

In addition, the hemisuccinate tris(hydroxymethyl) aminomethane derivatives of the 5β steroids and DHEA mentioned above are also expected to behave as rigid lipids. Other derivatives of the 5β steroids that are active may also be admixed with the lipid portion of the liposome or serve as components of the liposome. Thus for example 16 methylene β ET and 16 methylene β ET palmitate both disclosed in U.S. Pat. No. 4,602,008 which is herein incorporated by reference, may be used as components of the lipid portion of the liposome according to the invention.

Alternatively, a different form of versicle based on alpha tocopherol may be employed in the formulation according to the invention. The alpha tocopherol vesicles are formed using conventional means form an organic acid derivative of alpha tocopherol. Organic acids which can be used to derivatize the alpha tocopherol include the carboxylic acids, dicarboxcylic acids, poly carboxylic acids, hydroxy acids, amino acids and polyamine acids. The Derivatives may be the esters or hemiesters of the forgoing acids. In addition the organic acid may be provided as the salt of the corresponding acid or may be converted to the salt. Such salt forms increase the water solubility of the organic acid and thus provide a stronger gradient driving the formation of the bilayer essential to the formation of the liposome.

Water soluble organic acids are useful in connection with the alpha tocopherol derivative. Water soluble aliphatic carboxylic acids such as acetic propionic butyric valeric acids and the like, water soluble aliphatic dicarboxcylic acids such as malonic, succinic, glutaric adipic, pimelic, maleic and the like, and water soluble aromatic dicarboxylic acids such as hemimeilitic, trimesic, succinimide and the like, water soluble hydroxy acids such as glycolic, lactic, mandelic, glyceric, malic, tartaric, citric and the like; and any of the amino acids and poly amino acids.

The salt forms of the drivatized alpha tocopherol can be prepared by dissolving in an appropriate volatile solvent, the organic acid derivative of the alpha tocopherol and the counter ion of the salt, for example the free base of the salt, followed by removal of the solvent by evaporation leaving a residue consisting of the salt form of the organic acid. The counter-ions that may be used include for example, tris, 2-amino-2-methyl-1-3-propanediol, 2-amino ethanol, bis-tris propane, triethanolamine and the like.

Thus, the 3α ET, 3β ET or DHEA, as the case may be, may be esterified at the 3 carbon of the steroid ring structure with a dicarboxylic acid, such as for example succinate. When esterified the remaining carboxylic acid moiety may be either free or as a salt thereof. Also optionally included in the components making up the lipid bilayer are the organic acid derivatives of the 5β steroids and DHEA as described herein above.

The 5β steroids. DHEA and their derivatives are essentially insoluble in water and may be incorporated into alpha tocopherol or other lipid vesicles by entrapment because the 3β steroid is expected to partition into the alpha-tocopherol bilayers. The 5β steroid is dissolved in an appropriate organic solvent which is then evaporated leaving a film or residue of the compound. When an aqueous suspension of the previously formed liposomes is added to the residue, the residue will be entrapped in the lipid bilayer of the liposome. In this situation, uni-lamellar vesicles or liposomes are used; if multi- lamellar vesicles or liposomes are used the 5β steroid may be entrapped only in the outer layer and the internal layers of the lipid or alpha tocopherol contain none of the steroid.

Compositions accoring to the invention utalizing tris salts of cholesterol hemisuccinate for the lipid envelope and the 5β steroid or DHEA or their water insoluble derivatives incorporated therein are generally formed using the same methods as described above for the alpha tocopherol based liposomes.

In all the prior art liposomes the sterol derivative or alpha tocopherol derivative functions not as an active agent exerting a biological effect, but as the delivery mechanism for some other, generally water-insoluble, but biologically active compound. Thus for example, U.S. Pat. Nos. 5,041,278 and 5,231,112 both to Janoff et al., both show the use of the cholesterol derivatives and alpha tocopherol derivatives to deliver water insoluble anti-fungal agents such as miconazol and itraconazol In the present invention, the therapeutic 5β steroid as an ester of an organic acid is a structural part of the lipid envelope rather than a vehicle for delivering another compound. By using the 5β steroid and its derivatives as both the liposome structural component and as the active agent, it is possible to eliminate the administration of additional steroid and steroid derivatives or lipids iv to a patient. As the 5β steroids are active anti-obesity agents, by eliminating the use of additional steroid and lipids as part of the delivery vehicle, the obese patient is spared the health risk of exposure to additional circulating lipids and steroids. Furthermore, by eliminating additional lipids and steroids as part of the delivery vehicle, circulating lipid levels in obese patients are not artificially elevated, making the monitoring of lipid levels in these patients easier and more accurate.

The liposomes described herein above may be used to entrap therein a water soluble compound or compounds, a partially water soluble compound or a water- insoluble compound, using a number of different approaches. The general methods described herein are useful whether the liposome is of the conventional lipid bi-layer type, based on alpha tocopherol-organic acids (or salts thereof) or cholesterol hemisuccinate (or salts thereof), any of which may contain the 5β steroid partitioned therein. Equally the general methods are useful if the liposome envelope is produced from a 5β steroid or derivative of the 5β steroid, such as an organic acid ester of the 5β steroid which may be expected to form a bilayer. (For purposes of the description immediately following the compounds forming the bi-layer envelope of the liposome or liposome—like structure whether conventional, alpha tocopherol (and derivative)—based, cholesterol hemisuccinate or 5β steroid (and derivative)-based is referred to as the "bilayer".)

Compounds that partition into the bilayer or water soluble compounds may be added to the aqueous phase before formation of the vesicles to entrap the agent within the vesicles during formation. Alternatively, compounds which are water-insoluble or lipid soluble may be added to the suspension of bilayer vesicles after the vesicles are formed, in which case the compound partitions into the bilayer. In another embodiment, a water insoluble compound and the salt form of and organic acid derivative may be added to an organic solvent so that both are solubilized. The organic solvent may then be evaporated, leaving a film containing a homogeneous distribution of the water-insoluble compound in the bilayer. Bilayer vesicles entrapping the water insoluble compound or compounds are then formed when an aqueous buffer is added to the film with agitation. Such vesicles may then be sonicated forming unilamellar vesicles.

The bilayer forming the vesicles of the present invention are advantageous when used to entrap water insoluble bio-active agents or those that are sparingly soluble in water. In this regard the non-derivative forms of the 5β steroids may be entrapped in the bilayer. Thus α ET, β ET, ED, DHEA each individually or in a mixture of two or more may be added to the bilayer vesicles after the vesicles are formed to partition into the bilayer. Alternatively, α ET, β ET, ED, DHEA each individually or in a mixture of two or more may be added to the solvent containing the compounds which will form the bilayer. When the solvent is removed by evaporation or other means to form a film the α ET, β ET, ED, DHEA or mixture thereof is contained in a homogenous distribution in the bilayer. Following agitation and or sonication in an aqueous buffer, vesicles are formed. Using this approach alpha tocopherol hemisuccinate or cholesterol hemisuccinate or conventional lipids which additionally comprise individually α ET, β ET, ED, DHEA or mixture two or more of these 5β steroids may be formed.

Alternatively, one or more of the derivatives of the 5β steroids may be used to form the bilayer of the vesicles of the present invention. In particular esters of organic acid acids and any of the 5β steroids may be produced and a bilayer vesicle formed therefrom as described above. Such organic acid derivatives include but are not limited to esters of organic acids and 5β-androstan-3α, 11α-diol-17-one, 5β-androstan-3β, 11β-diol-17-one, 5β-androstan-3α, 11β-diol-17-one, 5β-androstane-11α-ol-3,17-dione, 5β-androstane -11β-ol-3,17-dione, 5β-androstane-3α,16α-diol-17-one, wherein the ester is formed between the organic acid and the carbon at 11, or 16 hydroxyl group. Furthermore, 16-methyl-7-hydroxy-5β-androstan-3-ol-17-one may be esterified with an organic acid at the 7 hydroxy group to yield the corresponding derivative. In addition similar esters may be formed between the organic acid and the carbon at the 3 hydroxy group of α ET, β ET or DHEA. The organic acid may be any of the organic acids listed herein above, for example the dicarboxylic acid succinate may be used yielding the hemisuccinate derivative of the corresponding 5β steroid. Some of the organic acid derivatives of the 5β steroids are commercially available including but not limited to 5β- androstan-3α-ol-17-one 3-hemisuccinate and 5β-androstan-3β-ol-17-one 3-hemisuccinate.

The ester, derivative of the 5β steroid if used to form the bilayer of the vesicles of the present invention may be formed completely of the ester derivative, or a mixture of the ester derivative of the 5β steroid and other lipids or the alpha tocopherol or cholesterol hemisuccinate. Likewise, the bilayer formed of any of the ester derivatives of the 5β steroids, may be used to further include and deliver non-derivative forms of the 5β steroids which may be entrapped in the bilayer. Thus α ET, β ET, ED, DHEA each individually or in a mixture of two or more may be added to the bilayer vesicles made of the ester derivative of the 5β steroid after the vesicles are formed to partition into the bilayer. Alternatively, α ET, β ET, ED, DHEA each individually or in a mixture of two or more may be added to the solvent containing the ester derivative of the 5β steroid which will form the bilayer. When the solvent is removed by evaporation or other means to form a film, the α ET, β ET, ED, DHEA or mixture thereof is contained in a homogenous distribution in the bilayer. Following agitation and or sonication in an aqueous buffer, vesicles are formed. Using this approach bilayers formed from ester derivatives of the 5β steroids which additionally comprise individually α ET, β ET, ED, DHEA or mixtures of two or more of these 5β steroids may be formed.

All of the above-described liposomes may additionally be used to envelop and contain an aqueous phase within the liposome. The aqueous phase may also have dissolved or suspended therein al therapeutic agent. In the present invention the aqueous phase may also advantageously contain an anti-obesity effective product that is water soluble. In particular the protein which is the protein product encoded by the ob gene in mice and its human equivalent, or any anti-obesity effective fragment thereof, which are soluble in phosphate buffered shine may be dissolved in the aqueous phase within the liposome according to the invention. If the protein porduct encoded by the ob gene or its human equivalent is used a pH of 7.4 is preferred. The aqueous phase containing the protein may be incorporated into the liposome, whether unilamellar, multilameller, LUVET or otherwise by conventional means. Preferably the method will produce a high capture volume of the aqueous phase and the protein dissolved therein.

The following examples will be understood by those ordinarily skilled in the aret to be exemplry of the invention and are not intened to be limiting.

EXAMPLE I

Preparation of Liposome Vesicles Containing α ET

A. Vesicles Containing α Tocopherol Hemisuccinate and α ET

1. Preparation of the Tris Salt of Alpha Tocopherol Henisuccinate

Five gramns of alpha tocopherol hydrogen succinate (Sigma Chemical co., St. Louis, Mo.) are dissolved in 100 ml of diethyl ether. Tris base (Fisher, Fair Lawn N.J.)(1.14 g) dissolved in about 5 ml of water was then added in 0.5 ml portions to the ether solution while stirring or shaking. The solution was rotoevaporated to dryness and then further dried under high vacuum to produce the Tris salt of alpha tocopherol Hemisuccinate.

2. Production of Cholesterol Hemisuccinate Tris Salt

Cholesterol hydrogen succinate 50.3 g, 0.11 moles (ICN, Cleveland Ohio) is dissolved in 1.5 liters of dilethyl ether, Tris base (12.1 g, 0.1 moles (Fisher, Fairlawn, N.J.) Is dissolved in 30 ml of water. The Tris solution is added to the cholesterol solution and the resulting solution is rotoevaporated to a milky wet residue. This residue is freeze dried for 12 hours an the cholesterol hemisuccinate Tris salt product is recrystallized three times from about 5 liter volumes of boiling ethyl acetate.

The boiling ethyl acetate solution is filtered hot and cooled to room temperature. A gel-like cholesterol hemisuccinate Tris salt appears which is filtered through a 1000 ml sintered glass funnel and the ethyl acetate is removed by squeezing and mechanical compression. Further solvent removal is accomplished under 0.1 mm Hg vacuum for 12 hrs to yield a hard brittle white material weighing approximately 23 grams. The disk is pulverized in a mortar and pestle and trace amounts of ethyl acetate are removed by heating to 50° C. and applying a 0.1 mm Hg vacuum.

3. Solubilization of α ET

Fifty milligrams of alpha tocopherol hemisuccilnate Tris salt, 50 mg of cholesterol hemisuccinate Tris salt, (prepared as above) and 20 mg of α ET (Research Plus, Bayonne N.J.) are added to an excess amount of methanol and dried under vacuum in a round bottom flask. The resulting film is then resuspended in 1.0 ml of 10 mM Tris-HCl buffer with agitation in the presence of glass beads to increase mixing until a gel forms. The gel is sonicated to yield 0.2–0.4 micron diameter vesicles.

B. Liposome Vesicles Containing Cholesterol Hemisuccinate Tris Salt and α ET 100 mg of cholesterol hemisuccinate Tris Salt and 20 mg of α ET are added to an excess amount of methanol and dried under vacuum in a round bottom flask. The resulting film is then resuspended in 1.0 ml of 10 mM Tris-HCl buffer with agitation in the presence of glass beads to increase mixing until a gel forms. The gel is sonicated to yield 0.2–0.4 micron diameter vesicles containing I α ET.

EXAMPLE II

Preparation of Liposome Vesicles Containing β ET

A. Liposome Vesicles Containing α Tocopherol Henisuccinate and β ET

Liposome Vesicles containing α tocopherol hemisuccinate and β ET are prepared as above in Example I, steps A 1., A 2., and A 3., except that 20 mg of β ET (Research Plus, Bayonne N.J.) are used instead of α ET.

B. Liposome Vesicles Containing Cholesterol Hemisuccinate and β ET

Liposome vesicles containing cholesterol hemisuccinate and β ET are prepared as above in Example I, step B except that 20 mg of β ET are used instead of α ET.

EXAMPLE III

Preparation of Liposome Vesicles Containing ED

A. Liposome Vesicles Containing α Tocopherol Hemisuccinate

Liposome Vesicles containing a tocopherol hemisuccinate and ED are prepared as above in Example I, steps A 1., A 2., and A 3., except that 20 mg of ED (Research Plus, Bayonne N.J.) are used instead of α ET.

B. Liposome Vesicles Containing Cholesterol Hemisuccinate and ED

Liposome vesicles containing cholesterol hemisuccinate and ED are prepared as above in Example I, step B except that 20 mg of ED are used instead of α ET.

EXAMPLE IV

Preparation of Liposome Vesicles Containing α ET Hemisuccinate

A. Preparation of Liposome Vesicles Containing α Tocopherol Hemisuccinate and α ET Hemisuccinate 1. Preparation of the Tris Salt of 5β Androstan-3α-ol-17-one 3 Hemisuccinate 5β androstan-3α-ol-17-one 3 hemisuccinate (herein after 5α ET 3-hemisuccinate), 39 .g, 0.1 moles, (Research Plus, Inc.) is dissolved in 1.5 liters of diethyl ether, Tris base (12.1 g, 0.1 moles ( Fisher, Fairlawn, N.J.) Is dissolved in 30 ml of water. The Tris solution is added to the 5α ET 3-hemisuccinate solution and the resulting solution is rotoevaporated to a milky wet residue. This residue is freeze dried for 12 hours and the 5α ET 3-hemisuccinate Tris salt product is recrystallized three times from about 5 liter volumes of boiling ethyl acetate.

The boiling ethyl acetate solution is filtered hot and cooled to room temperature. A gel-like 5α ET 3-hemisuccinate Tris salt appears which is filtered through a 1000 ml sintered glass funnel and the ethyl acetate is removed by squeezing and mechanical compression. Further solvent removal is accomplished under 0.1 mm Hg vacuum for 12 hrs to yield a hard brittle white material weighing approximately 23 grams. The disk is pulverized in a mortar and pestle and trace amounts of ethyl acetate are removed by heating to 50° C. and applying a 0.1 mm Hg vacuum.

2. The Tris salts of alpha tocopherol hemisuccinate is prepared as in Example I Step A 1. Fifty milligrams of alpha tocopherol hemisuccinate Tris salt, 55 mg of α ET hemisuccinate Tris salt prepared as above are added to an excess amount of methanol and dried under vacuum in a round bottom flask. The resulting film is then resuspended in 1.0 ml of 10 mM Tris-HCl buffer with agitation in the presence of glass beads to increase mixing until a gel forms. The gel is sonicated to yield 0.2–0.4 micron diameter vesicles.

EXAMPLE V

Preparation of Liposome Vesicles Containing α Tocopherol Hemisuccinate and β ET Hemisuccinate A. Preparation of the Tris Salts of 5β androstan-3β-ol-17-one 3 hemisuccinate (hereinafter β ET hemisuccinate)

The Tris salt of β ET hemisuccinate is prepared as in Example IV A 1 except that 5β androstan-3β-ol-17-one 3 hemisuccinate is used instead of 5β androstan-3α-ol-17-one 3 hemisuccinate.

B. Preparation of the Liposome of Alpha Tocopherol Hemisuccinate Tris Salt and B et Hemisuccinate Tris Salt The liposome of alpha tocopherol hemisuccinate Tris salt and β ET hemisuccinate Tris salt is prepared as above in Example IV A 2 except that the Tris salt of β ET hemisuccinate is used in stead of the Tris salt of ET hemisuccinate.

EXAMPLE VI

Liposome Vesicles Containing α ET Hemisuccinate and β ET Hemisuccinate

The Tris salt of 5β androstan-3α-ol-17-one 3 hemisuccinate is prepared as in Example IV. A. 1.

The Tris salt of 5β androstan-3α-ol-17-one 3 hemisuccinate is prepared as in Example V. A.

The liposome vesicles containing the Tris salt of α ET hemisuccinate and Tris salt of β ET hemisuccinate are prepared as in Example IV A 2 except that the Tris salt of β ET hemisuccinate is used instead of the Tris salt of alpha tocopherol.

EXAMPLE VII

Preparation of Liposome Vesicles Containing α ET Hemisuccinate or β ET Hemisuccinate and α ET or β ET or ED A. Liposome Vesicles Containing α ET Hemisuccinate Tris Salt and α ET or β ET or ED 1. α ET Hemisuccinate Tris Salt and α ET α ET Hemisuccinate Tis Salt is prepared as above. 100 mg of α ET hemisuccinate Tris Salt and 20 mg of α ET are added to an excess amount of methanol and dried under vacuum in a round bottom flask. The resulting film is then resuspended in 1.0 ml of 10 mM Tris-HCl buffer with agitation in the presence of glass beads to increase mixing until a gel forms. The gel is sonicated to yield 0.2–0.4 micron diameter vesicles containing α ET.

2. αET Hemisuccinate Tris Salt and β ET

The vesicles are produced as in Example VII A. 1., except the β ET is used instead of α ET.

3. α ET Hemisuccinate Tris Salt and ED

The vesicles are produced as in Example VII A. 1., except the ED is used instead of α ET.

B. Liposome Vesicles Containing β ET Hemisuccinate Tris Salt and α ET or β ET or ED 1. β ET Hemisuccinate Tris Salt and α ET β ET Hemisuccinate Tris Salt is prepared as above. 100 mg of β ET hemisuccinate Tris Salt and 20 mg of α ET are added to an excess amount of methanol and dried under vacuum in a round bottom flask. The resulting film is then resuspended in 1.0 ml of 10 mM Tris-HCl buffer with agitation in the presence of glass beads to increase mixing until a gel forms. The gel is sonicated to yield 0.2–0.4 micron diameter vesicles containing α ET.

2. β ET Hemisuccinate Tris Salt and β ET

The vesicles are produced as in Example VII B.1. except the β ET is used instead of α ET.

3. β ET Hemisuccinate Tris Salt and ED

The vesicles are produced as in Example VII B.1. except the ED is used instead of α ET.

EXAMPLE VIII

Production of Liposomes Containing the 5β Steroid, Tris Salts of 5β Steroids and the Protein of the ob Gene.

A. Production of the Protein of the ob Gene

The protein of the ob gene is produced as described in M. A. Pellymounter, et al., Science, 269, 540 (1995). Briefly, The OB-coding sequence of the mouse and human ob genes terminal to the signal sequence (nt 178–612) are subcloned into a suitable expression vector such as PET 15b and over expressed in *E.coli* [BL21 (DE3)pIYsS] through the use of the T7 RNA polymerase system. Cells are grown at 30° C. to an absorbance at 595 nm of 0.7, induced with 0.5 mM isopropyl-β-D-thiogalactopyranoside over night, and collected by low-speed centrifugation. The cells are lysed in three freeze thaw cycles and digested with deoxyribonuclease I. Membranes are sonicated and extracted by detergent solubilization, and the final inclusion body sediment is dissolved in 6 M guanidine-HCl, 20 mM (pH 8.4).

Recombinant proteins were purified with denaturation by immobilized metal affinity chromatography (UMAC) with a Ni-ion affinity column and elution with increasing amounts of imidazole. Purified denatured OB protein was stored in g M guanidine- HCl, 10 mM sodium acetate (pH 5.0) and reduced with 1 mM dithiothreitol at room temperature of 1 hour.

The reduced protein is renatured with 20% glycol, 5 mM $CaCl_2$, 5 mM sodium acetate (pH 5.0), thorough mixing, and incubation at room temperature for 8 to 12 hours. After renaturation, the pH was adjusted to 8.4 by addition of Tris to 10. mMK and the hexahistidine tag was removed by thrombin cleavage. Cleaved, renatured protein was repurified by IMAC too separate product from thrombin and uncleaved fusion protein. Cleaved, renatured protein elutes from the Ni-ion affinity column at 40 mM imidazole, whereas thrombin is not retained, and uncleaved fusion protein elutes at 0.2 M imidazole. Product was then concentrated, treated with 100 mM EDTA and 10 mM potassium ferricyanide and further purified by gel filtration with a Pharmacia Superdex 7S 16/80 Column. The purified protein is dissolved in phosphate buffered saline (pH 7.4) at a concentration of 0.6 mg/ml.

Production of Liposomes

Each of the liposomes described in examples I–VI is prepared as above except that in place of 1.0 ml of 10 mM Tris-HCl buffer, 1.0 ml of PBS pH 7.4 containing 0.6 mg ml of OB protein is used.

In administration of the the liposomal dosage form of the present invention, the average daily dosage of the 5β steroid will range broadly between about 0.1 to about 100 mg/kg and preferably between about 0.1 and 10 mg/kg body weight. Similarly, the amount of the OB protein will be between 0.01 mg and 10 mg/kg.

While particular formulations for the liposomes comprising the 5β steroids with or without the OB protein are described herein, it is believed by the inventors that a parenteral liposome formulation including the 5β steroid and OB protein in a suitable injection vehicle is preferred, to utalize the different mechanisms of the two active agents to maximum benefit. While a parenteral route of delivery for the formulation is preferred, suspensions may also be made using the formulation of the invention which may be suitable for oral administration and increased up take of the 5β steroid.

While particular formulations of the liposome have been described herein, other liposomal formulations using similar and different lipid or lipid like components may be used in formulation according to the invention to deliver the 5β steroids without departing from the spirit of the invention.

We claim:

1. A pharmaceutical formulation comprising:
   a liquid injectable vehicle for parenteral administration;
   liposomes; and
   a pharmaceutically effective amount of a 5-β steroid.

2. The pharmaceutical formulation of claim 1 wherein said 5-β steroid is 5-β-androstane-3,17 dione.

3. The pharmaceutical formulation of claim 1 wherein said 5-β steroid is 3α-hydroxy-5-β-androstane-17-one.

4. The pharmaceutical formulation of claim 1 wherein said 5-β steroid is 3β-hydroxy-5-β-androstane-17-one.

5. The pharmaceutical formulation of claim 1 wherein said liposomes comprise an anti-obesity effective amount of an anti-obesity peptide or protein.

6. The pharmaceutical formulation of claim 5 wherein said 5-β steroid is 5-β-androstane-3,17 dione.

7. The pharmaceutical formulation of claim 5 wherein said 5-β steroid is 3α-hydroxy-5-β-androstane-17-one.

8. The pharmaceutical formulation of claim 5 wherein said 5-β steroid is 3β-hydroxy-5-β-androstane-17-one.

9. The pharmaceutical formulation of claim 5 wherein said anti-obesity peptide or protein is the expression product of the ob gene.

10. The pharmaceutical formulation of claim 9 wherein said 5-β steroid is 5-β-androstane-3,17 dione.

11. The pharmaceutical formulation of claim 9 wherein said 5-β steroid is 3α-hydroxy-5-β-androstane-17-one.

12. The pharmaceutical formulation of claim 9 wherein said 5-βsteroid is 3β-hydroxy-5-β-androstane-17-one.

13. The pharmaceutical formulation of claim 1, wherein the 5-β steroid is esterified with one of the carboxylic acid moieties of a dicarboxylic acid and the other carboxylic acid moiety being free or as a salt thereof.

14. The pharmaceutical formulation of claim 1 wherein the amount of said 5-β steroid is within the dosage range between about 1 and about 1000 mg per dosage form.

15. The pharmaceutical formulation of claim 1 wherein said said 5-β steroid is 16-alkylated 5β-androstane-3-diol-17-one or 16-alkylated 5β-androstane-3,7 diol-17-one.

16. A method for treating a condition selected from the group consisting of obesity, diabetes syndrome, diabetes associated with hypercordicoidism and combination thereof, and bone marrow suppressive disorders comprising:
   parenterally administering to a mammal in need of such treatment a pharmaceutical formulation comprising
   a liquid injectable vehicle for parenteral administration;
   liposomes; and
   a pharmaceutically effective amount of a 5-β steroid for treating obesity, diabetes or hypercorticoidism land combinations thereof.

17. The pharmaceutical formulation of claim 1, wherein the liposome comprises a lipid selected from the group consisting of alpha tocopherol, cholesterol and carboxylic acid derivatives thereof.

18. The pharmaceutical formulation of claim 17, wherein the weight ratio between the 5-β steroid and the lipid is between about 1:2 and 1:1000.

* * * * *